US008485967B2

(12) United States Patent
Takahashi et al.

(10) Patent No.: US 8,485,967 B2
(45) Date of Patent: Jul. 16, 2013

(54) ENDOSCOPIC IMAGING DEVICE AND ENDOSCOPE APPARATUS HAVING A CONFIGURATION TO PREVENT CONDENSATION

(75) Inventors: Kazuaki Takahashi, Kanagawa (JP); Yuichi Torii, Kanagawa (JP); Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 241 days.

(21) Appl. No.: 13/022,668

(22) Filed: Feb. 8, 2011

(65) Prior Publication Data

US 2011/0245608 A1 Oct. 6, 2011

(30) Foreign Application Priority Data

Mar. 31, 2010 (JP) .................................. 2010-084418

(51) Int. Cl.
*A61B 1/04* (2006.01)
(52) U.S. Cl.
USPC .......................... 600/169; 600/129; 600/109
(58) Field of Classification Search
USPC .......... 600/109, 129, 169, 176, 170; 359/507, 359/512; 348/340; 433/30, 31
See application file for complete search history.

(56) References Cited

U.S. PATENT DOCUMENTS

| 4,567,543 | A | * | 1/1986 | Miniet ........................... 361/749 |
| 6,000,959 | A | * | 12/1999 | Curtindale et al. ............ 439/247 |
| 6,135,969 | A | * | 10/2000 | Hale et al. ...................... 600/595 |
| 7,455,637 | B2 | * | 11/2008 | Takahashi ...................... 600/169 |
| 7,976,459 | B2 | * | 7/2011 | Laser .............................. 600/109 |
| 8,142,351 | B2 | * | 3/2012 | Aono et al. .................... 600/167 |
| 8,172,409 | B2 | * | 5/2012 | Nagamizu ...................... 359/512 |
| 2003/0089702 | A1 | * | 5/2003 | Carver et al. ................. 219/543 |
| 2007/0073108 | A1 | * | 3/2007 | Takahashi ...................... 600/169 |
| 2008/0091064 | A1 | * | 4/2008 | Laser .............................. 600/109 |
| 2011/0074941 | A1 | * | 3/2011 | Takasaki ......................... 348/68 |
| 2011/0118548 | A1 | * | 5/2011 | Kim et al. ....................... 600/109 |

FOREIGN PATENT DOCUMENTS

JP 2007-260190 A 10/2007

* cited by examiner

*Primary Examiner* — John P Leubecker
(74) *Attorney, Agent, or Firm* — Sughrue Mion, PLLC

(57) ABSTRACT

An endoscopic imaging device includes an objective optical system, an imaging element, a transmissive protective substrate, an optical member, and a circuit board. The objective optical system imports observation light from a subject. The imaging element captures an image of the observation light. The transmissive protective substrate is disposed on an imaging surface of the imaging element with an air gap interposed therebetween. The optical member is disposed between the objective optical system and the transmissive protective substrate to guide light from the objective optical system to the imaging surface. The circuit board is disposed so that an area where an electronic component is mounted faces the optical member and the electronic component is brought into contact with an outer surface of the optical member.

11 Claims, 7 Drawing Sheets

ENDOSCOPIC IMAGING DEVICE AND ENDOSCOPE APPARATUS HAVING A CONFIGURATION TO PREVENT CONDENSATION

CROSS-REFERENCE TO RELATED APPLICATIONS

This application is based upon and claims the benefit of priority from Japanese Patent Application No. 2010-084418, filed Mar. 31, 2010, the entire contents of which are incorporated herein by reference.

BACKGROUND

1. Technical Field

The present invention relates to an endoscopic imaging device and an endoscopic apparatus.

2. Related Art

An endoscope with a typical configuration has an elongated endoscope insertion portion to be inserted into a subject to be inspected, and an illumination optical system for illuminating an area to be observed and an imaging optical system for imaging the area to be observed are disposed in a front end portion of the endoscope insertion portion. In the illumination optical system, a light guide which is formed out of a bundle of optical fibers is provided to extend into the endoscope insertion portion, and a base end side of the light guide is coupled with a light source unit so that light from the light source unit can be guided to the front end portion of the endoscope and emitted as illumination light from the front end portion of the endoscope. In the imaging optical system, an objective lens is disposed in the front end portion of the endoscope, and an imaging element is disposed in the front end portion of the endoscope to be located in the position where the objective lens will focus an image. Thus, an observed image of the area to be observed is generated.

An example of the aforementioned endoscope includes an endoscope having an imaging device in which a triangular prism is disposed on an imaging surface of an imaging element with a transmissive protective substrate interposed therebetween (see JP-A-2007-260190). As described in JP-A-2007-260190, a heater is pasted to the triangular prism so as to prevent dew condensation from occurring in the transmissive protective substrate when the imaging element is powered on. In this configuration, the dew-condensation preventing heater which does not have any direct relation with imaging is still provided to be connected through a dedicated wiring from a peripheral circuit board or the like. Accordingly, there is a disadvantage that additional components are required in a manufacturing process, and there is a disadvantage that an extra installation space is required. In addition, the on/off timing of the heater must be controlled. Therefore, the configuration of the imaging device as a whole becomes complicated.

An object of the invention is to provide an endoscopic imaging device in which occurrence of dew condensation on a transmissive protective substrate is prevented with a simple configuration so that a good field of view is always secured, and an endoscopic apparatus having the endoscopic imaging device.

SUMMARY OF THE INVENTION

According to an aspect of the invention, an endoscopic imaging device includes an objective optical system, an imaging element, a transmissive protective substrate, an optical member, and a circuit board. The objective optical system imports observation light from a subject. The imaging element captures an image of the observation light. The transmissive protective substrate is disposed on an imaging surface of the imaging element with an air gap interposed therebetween. The optical member is disposed between the objective optical system and the transmissive protective substrate to guide light from the objective optical system to the imaging surface. The circuit board is disposed so that an area where an electronic component is mounted faces the optical member and the electronic component is brought into contact with an outer surface of the optical member.

According to the endoscopic imaging device and the endoscopic apparatus, the difference in temperature between the front and rear surfaces of a transmissive protective substrate which difference is a cause of dew condensation occurring on the transmissive protective substrate is reduced with a simple configuration, that is, by heating an optical member with heat generated from an electronic component mounted on a circuit board. Thus, occurrence of dew condensation is prevented so that a good field of view is secured.

DETAILED DESCRIPTION

An exemplary embodiment of the invention will be described in detail below with reference to the drawings.

Figure 1:
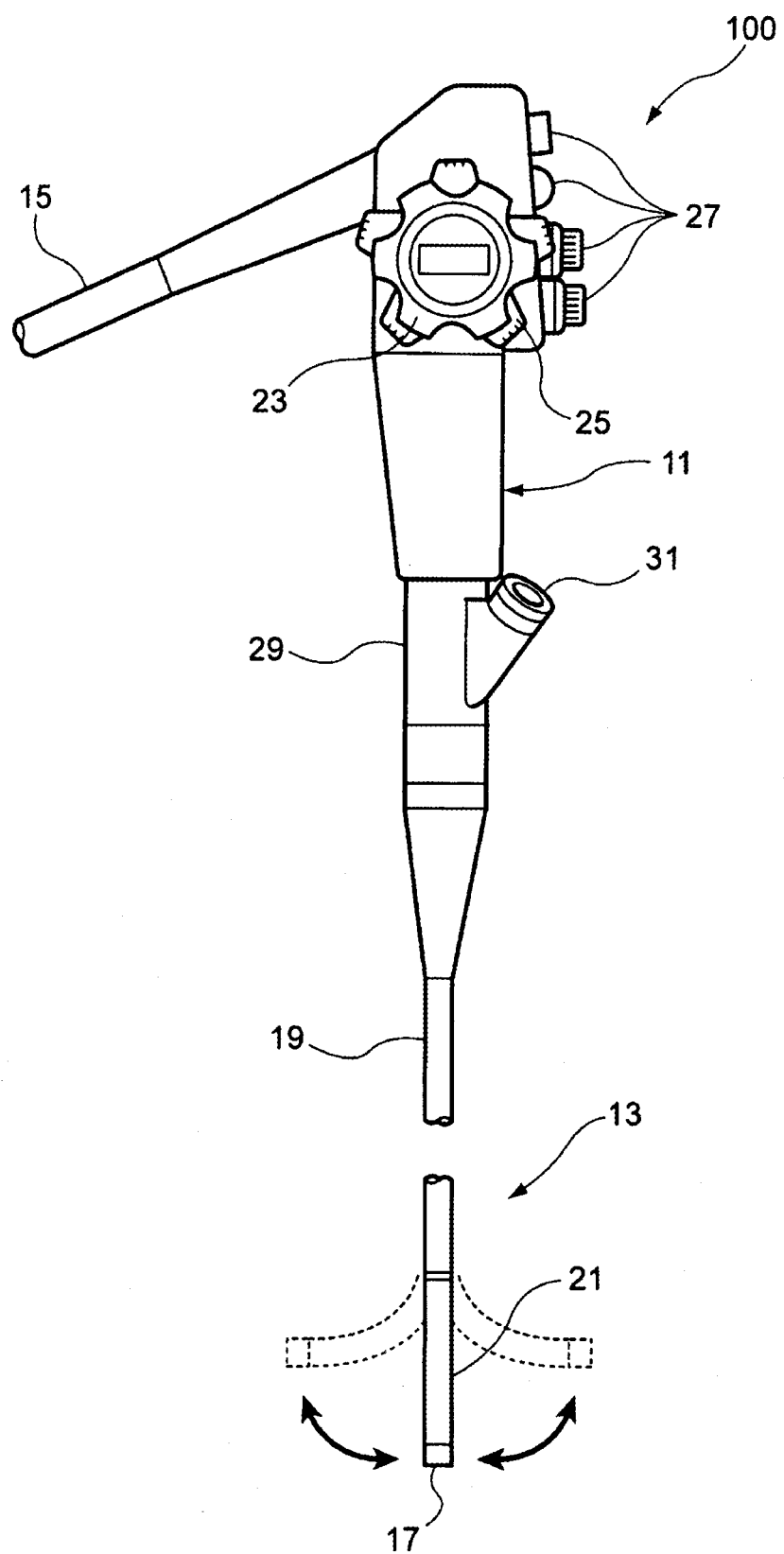
FIG. 1 is an overall configuration view of an endoscopic apparatus for the purpose of explaining an exemplary embodiment of the invention.

FIG. 1 is an overall configuration view of an endoscopic apparatus for the purpose of explaining the exemplary embodiment of the invention.

An endoscopic apparatus 100 has a body operation portion 11 and an endoscope insertion portion 13 which is provided consecutively to the body operation portion 11 and which will be inserted into a body cavity. A universal cable 15 is connected to the body operation portion 11, and a not-shown connector is provided in a front end of the universal cable 15. The connector is removably connected with a not-shown light source unit, by which illumination light is sent to an illumination optical system in a front end portion 17 of the endoscope insertion portion 13. A video connector is also connected to the connector. The video connector is removably connected with a processor which performs image signal processing or the like.

The endoscope insertion portion 13 is constituted by a soft portion 19, a curved portion 21 and the front end portion 17 in order of increasing distance from the body operation portion 11. The curved portion 21 can be operated to be curved remotely by rotation of angle knobs 23 and 25 of the body operation portion 11. Thus, the front end portion 17 can be directed in a desired direction.

In addition to the angle knobs 23 and 25, various buttons 27 such as an air-supply/water-supply button, a suction button, a shutter button, etc. are provided side by side in the body operation portion 11. In addition, a consecutive joint portion 29 extended toward the endoscope insertion portion 13 is provided with a forceps insertion portion 31. An operative instrument such as forceps inserted in the forceps insertion portion 31 is guided out through a forceps port 33 (see FIG. 2) which is formed in the front end portion 17 of the endoscope insertion portion 13.

Figure 2:
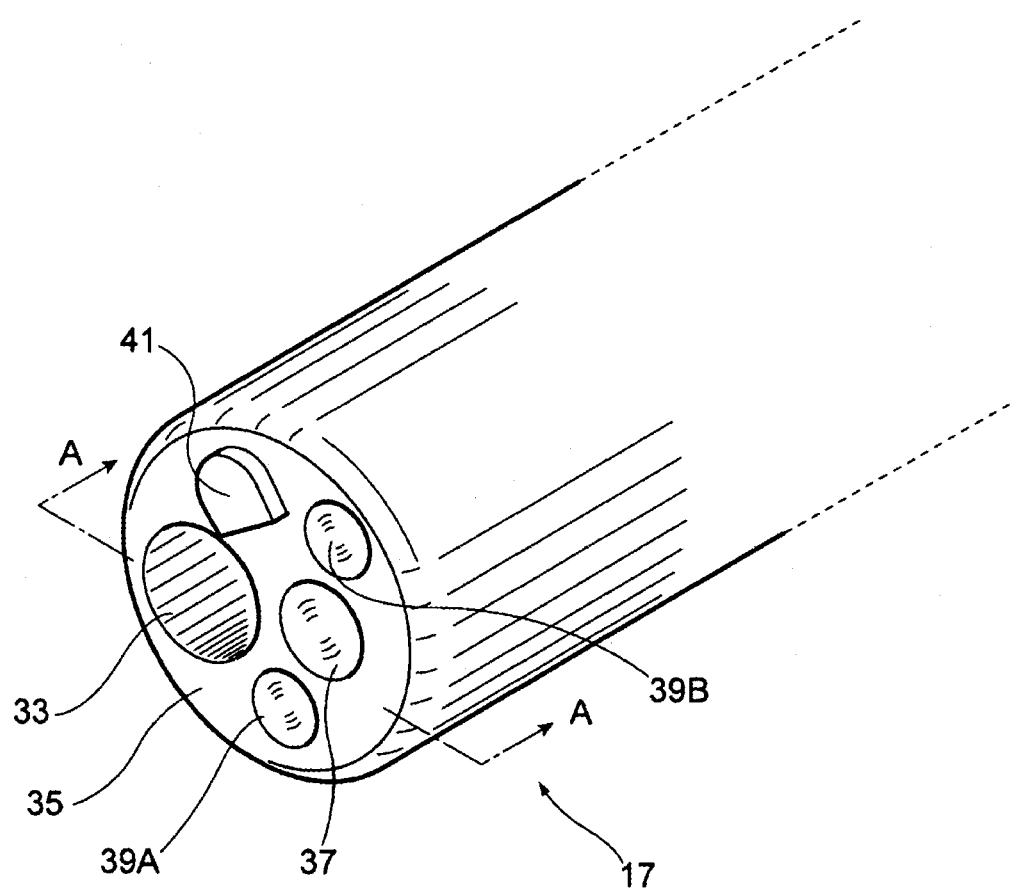
FIG. 2 is a schematic external view of a front end portion of an endoscope insertion portion.
Figure 3:
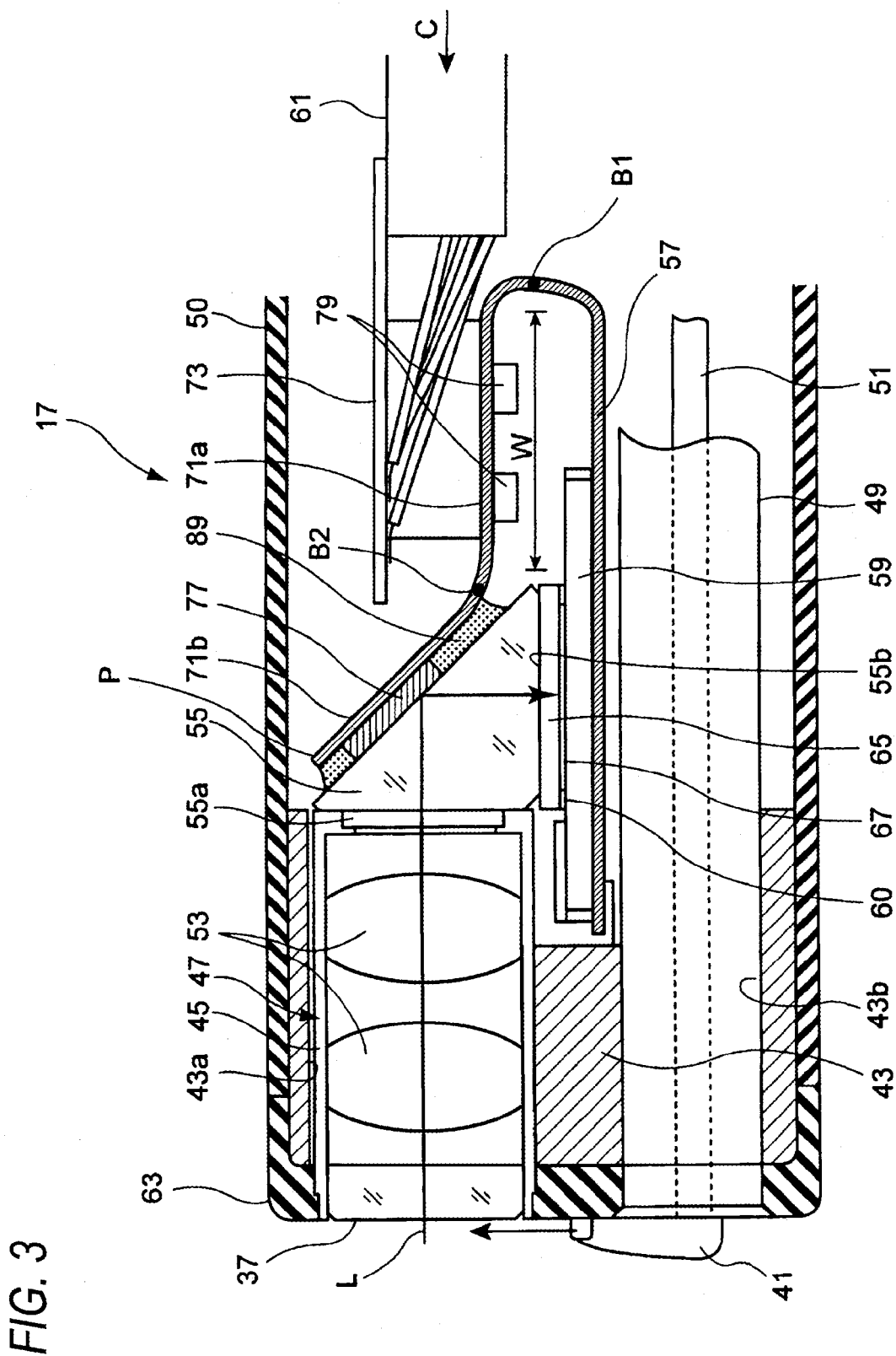
FIG. 3 is a sectional configuration view taken on line A-A in FIG. 2.

FIG. 2 is a schematic external view of the front end portion of the endoscope insertion portion, and FIG. 3 is a sectional configuration view taken on line A-A in FIG. 2.

As shown in FIG. 2, in the front end portion (hereinafter also referred to as endoscope front end portion) 17 which is the front end portion of the endoscope insertion portion 13, an observation window 37 of an imaging optical system is disposed in a front end surface 35 thereof, and irradiation holes 39A and 39B of an illumination optical system are disposed on opposite sides of the observation window 37. The forceps port 33 is disposed near the observation window 37 and the irradiation holes 39A and 39B. Further, a nozzle 41 for supplying air and water to the observation window 37 is disposed so that an ejection port thereof is directed toward the observation window 37.

As shown in FIG. 3, the endoscope front end portion 17 has a front end hard portion 43 made from a metal material such as a stainless steel material, an imaging portion 47 fixed to the front end hard portion 43 through a lens tube 45 fitted to a drilled hole 43a formed in the front end hard portion 43, and a forceps pipe 49 made from metal and disposed in another drilled hole 43b. In addition, the endoscope front end portion 17 receives an air-supply/water-supply pipe 51 connected to the nozzle 41, and various members connected to the illumination optical system, such as a not-shown light guide for guiding light.

In the imaging portion 47, the optical path of light imported through an objective lens group 53 consisting of a plurality of objective lenses received in the lens tube 45 is changed at right angles by a triangular prism 55, and formed as an image on an imaging element 59 mounted on a circuit board 57. Thus, an image signal based on image information imported by the imaging element 59 is outputted through the circuit board 57. The imaging optical system including the objective lens group 53, the triangular prism 55 and the imaging element 59 is disposed inside a housing of the endoscope front end portion 17 so as to serve as an imaging device. In addition, an illumination optical system is constituted by optical members such as lenses disposed in the irradiation holes 39A and 39B (see FIG. 2), and the light guide connected to the optical members. These members are also disposed inside the housing of the endoscope front end portion 17. The image information outputted from the imaging element 59 is transmitted to a not-shown processor through a signal cable 61 so as to be processed into an image for display.

A not-shown metal sleeve is connected to the outer circumference of the front end hard portion 43, and a not-shown node ring disposed in the curved portion 21 (see FIG. 1) is flexibly connected to the metal sleeve. The outer circumference of the metal sleeve is covered with a casing tube 50, and the front end side of the front end hard portion 43 is covered with a front end cover 63. The casing tube 50 and the front end cover 63 are bonded to each other tightly enough to prevent water from entering the inside thereof.

The objective lens group 53 is connected to an entrance-side end surface 55a of the triangular prism 55. A cover glass 65 serving as a transmissive protective substrate is bonded to an exit-side end surface 55b of the triangular prism 55. On the opposite side of the cover glass 65 to the side where the cover glass 65 is bonded to the triangular prism 55, the imaging element 59 is disposed with an air gap 67 interposed therebetween. The air gap 67 has a predetermined volume defined by a frame 60 disposed around the imaging element 59.

The circuit board 57 mounted with the imaging element 59 is bent back in a first bending axis B1 in FIG. 3. In a second bending axis B2, the circuit board 57 is further bent up from a horizontal plane illustrated in FIG. 3 and along a total reflection slope (hereinafter referred to as slope simply) of a periphery of the prism serving as a total reflection surface of the triangular prism 55, so as to press the slope of the triangular prism 55. Here, the triangular prism is used as an optical member for guiding light to the imaging element 59 by way of example. The optical member is not limited to the triangular prism, but an optical path changing member of another shape and another system may be used. The material of the cover glass 65 is not limited to a glass material but may be another material such as a translucent resin if it has transmittance with respect to observation light.

Here, the circuit board 57 will be described more in detail.

Figure 4:
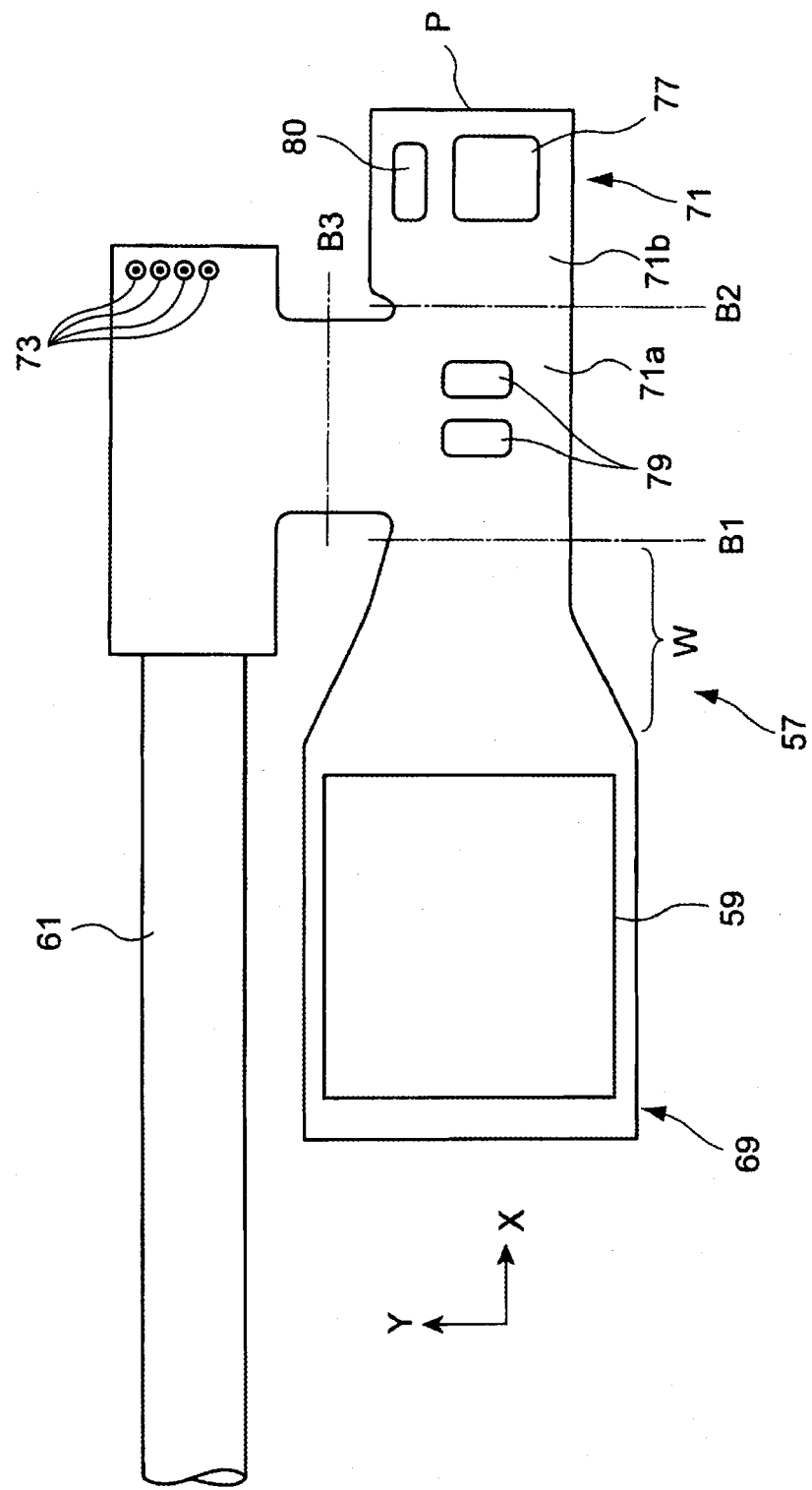
FIG. 4 is a plan view showing a developed state of a circuit board shown in FIG. 1.
Figure 5:
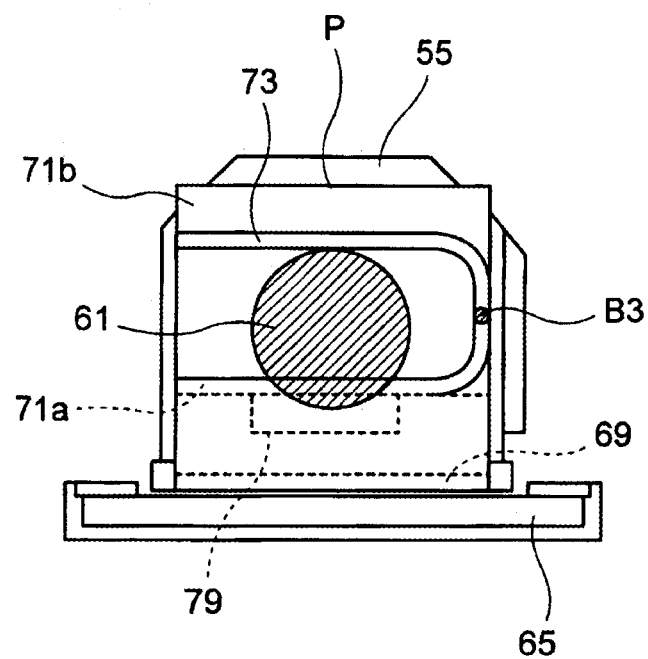
FIG. 5 is a view taken in the direction of arrow C, showing an imaging device in FIG. 3.

FIG. 4 is a plan view showing a developed state of the circuit board 57, and FIG. 5 is a view taken in the direction of arrow C, showing the imaging device in FIG. 3.

As shown in FIG. 4, the circuit board 57 is an FPC (Flexible Printed Circuit) board, which is sectioned into an imaging element mounting portion (first board portion) 69 where the imaging element 59 is mounted, a component mounting portion 71 which is provided continuously to the imaging element mounting portion 69 through the first bending axis B1 and the second bending axis B2 and where various electronic components are mounted, and a cable connection portion (fourth board portion) 73 which is provided continuously to the component mounting portion 71 through a third bending axis B3. The component mounting portion 71 is sectioned into a first component mounting portion (second board portion) 71a and a second component mounting portion (third board portion) 71b with the second bending axis B2 as a border.

In the imaging element mounting portion 69, the imaging element 59 is mounted on an upper surface side of the circuit board 57 shown in FIG. 4. The aforementioned frame 60 not shown and the glass cover 65 are disposed on an upper surface side of the imaging element 59.

In the component mounting portion 71, various electronic components 79, 80, etc. for driving and controlling the imaging element 59 are mounted. A regulator 77 which will be described later is mounted in the second component mounting portion 71b.

In the cable connection portion 73, lead wires of the signal cable 61 are connected to lands formed on the back side in FIG. 4 by soldering or the like respectively.

The circuit board 57 is bent in the first bending axis B1 as shown in FIG. 3, so that the electronic components 79 mounted on the first component mounting portion 71a face an area W which ranges from an edge portion of the imaging element mounting portion 69 on the component mounting portion 71 side to the first bending axis B1. On this occasion, the surface of the area W of the circuit board 57 is covered with an insulating layer so that insulation can be secured even if the electronic components 79 are disposed closely to the imaging element mounting portion 69. In addition, the electronic components 79 can be prevented from suffering radiant heat from other electronic components close to the electronic components 79 or from suffering influence of radiant noise.

In the circuit board 57, the second component mounting portion 71b is bent in the bending axis B2 and disposed along the slope of the triangular prism 55. Thus, of the electronic components mounted on the second component mounting portion 71b, the regulator 77 generating especially large heat abuts against the slope of the triangular prism 55.

On this occasion, since the circuit board 57 is bent in the bending axis B2, the regulator 77 and another electronic component 80 mounted on the second component mounting portion 71b are pressed onto the slope of the triangular prism 55 due to the elastic repulsion of the circuit board 57 itself. Then, a space between the second component mounting portion 71b and the slope of the triangular prism 55 is filled with a bonding agent so that a bonding agent layer 89 is formed to keep the regulator 77 and the other electronic component 80 in contact with the slope of the triangular prism 55. Thus, the regulator 77 and the other electronic component 80 are fixed in tight contact with the triangular prism 55 with no space therebetween, so as to be prevented from being separate from the slope of the triangular prism 55.

In addition, the wiring pattern of the circuit board 57 is made dense in the second bending axis B2 which is the border between the first component mounting portion 71a and the second component mounting portion 71b. Thus, the flexural rigidity in the second bending axis B2 is made higher than any other portion. As a result, the second component mounting portion 71b can press the triangular prism 55 more strongly, so as to improve the tight contact between the triangular prism 55 and the electronic components 77 and 80. Thus, the tight contact between the both can be kept surely till the bonding agent is solidified, and misalignment between the both can be also prevented.

Then, in the circuit board 57, the cable connection portion 73 is bent in the bending axis B3 as shown in FIG. 5, so that the signal cable 61 is put between the cable connection portion 73 and the first component mounting portion 71a. On this occasion, since a component non-mounting surface (rear surface opposite to the component mounting surface) of the first component mounting portion 71a facing the cable connection portion 73 is covered with an insulating layer, the insulation of lands etc. to which the signal cable 61 is connected can be improved.

Thus, as shown in FIG. 3, the circuit board 57 which has been bent into layers including the imaging element mounting portion 69 as a lowermost layer, the component mounting portions 71a and 71b as intermediate layers, and the cable connection portion 73 as an uppermost layer is fixed to the imaging element 59 and the triangular prism 55. In addition, in the circuit board 57, the bending axis B2 and the cable connection portion 73 are disposed not on a distal end P side but on an imaging element 59 side (lower side in FIG. 3) of the second component mounting portion 71b fixed to the triangular prism 55. The distal end P is an end of the second component mounting portion 71b which is far from the imaging element 59. When the circuit board 57 is bent back to have such a layout, the elastic repulsion of the second component mounting portion 71b in the bending axis B2 can be increased, and the installation space can be reduced.

Figure 6:
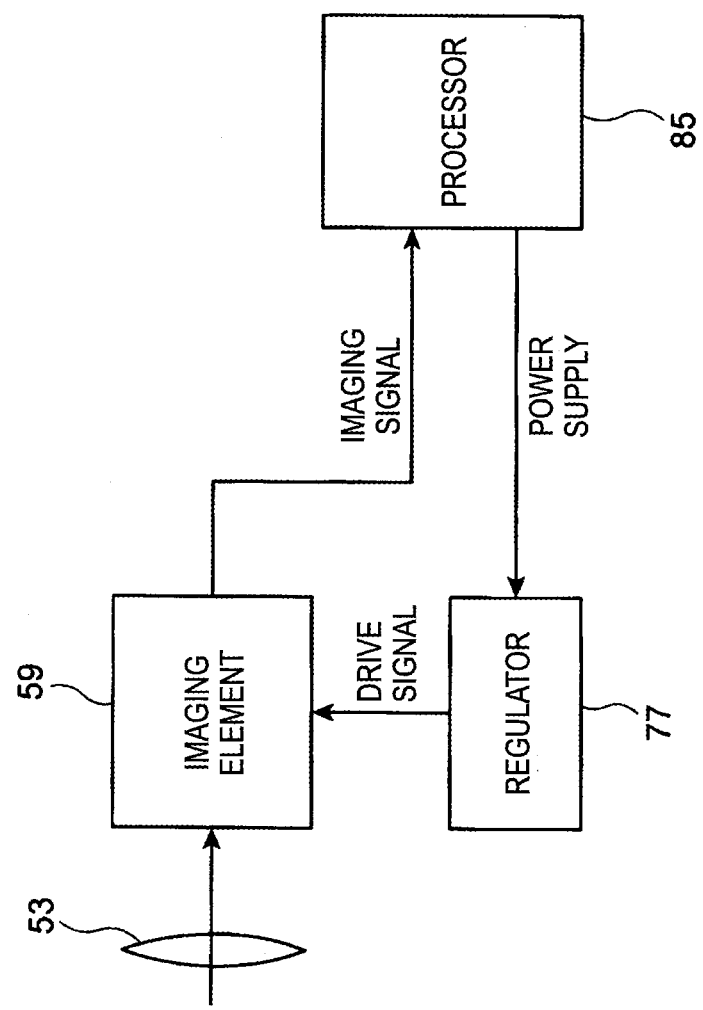
FIG. 6 is a circuit configuration diagram of an imaging element driving circuit which is applied to the endoscopic apparatus of FIG. 1.

Here, FIG. 6 shows a schematic connection circuit between the imaging element 59 and the regulator 77.

When electric power is supplied to the regulator 77 from a processor 85 connected to the endoscopic apparatus, the regulator 77 outputs a drive signal of a predetermined voltage level to the imaging element 59. The imaging element 59 receives the drive signal from the regulator 77 and outputs to the processor 85 an imaging signal of image information imported through the objective lens group 53. That is, the drive start timing of the regulator 77 is inevitably coincident with the drive start timing of the imaging element 59.

Description will be made below about behavior of temperature change in an imaging portion after the endoscopic apparatus 100 configured thus is powered on.

Figure 7:
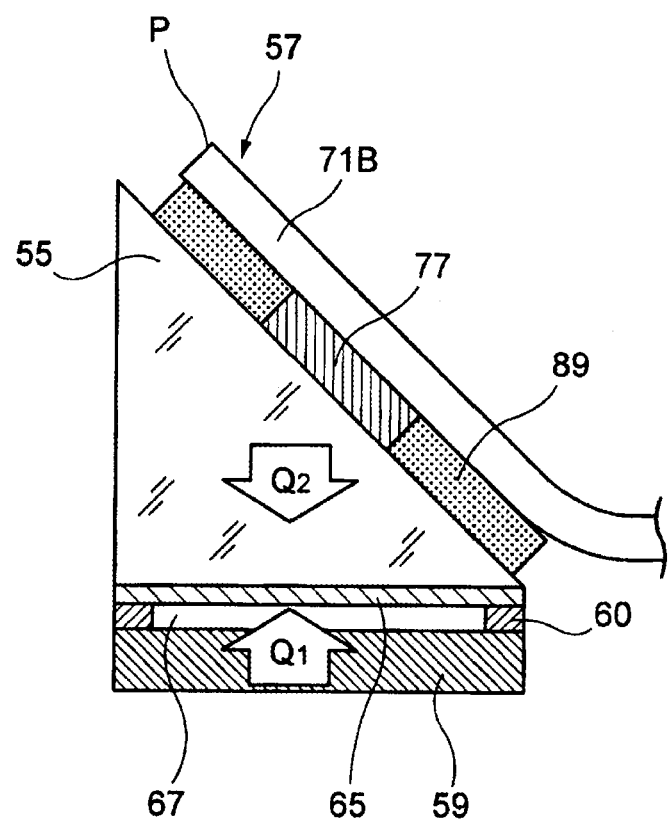
FIG. 7 is an explanatory view of temperature characteristics in the endoscopic apparatus of FIG. 1.

FIG. 7 is an enlarged view schematically showing an area including the imaging element and the triangular prism in the imaging portion.

In the endoscopic apparatus, as shown in FIG. 7, as soon as the processor is powered on, electric power is supplied to the regulator 77, and driving the imaging element 59 is started in sync therewith. Then, heat Q1 from the imaging element 59 and heat Q2 from the regulator 77 are generated concurrently and begin to be propagated to the surroundings. The heat Q1 from the imaging element 59 is transmitted to the cover glass 65 through media such as the air gap 67, the frame 60 etc. On the other hand, the heat Q2 from the regulator 77 is transmitted to the surroundings such as the cover glass 65 etc. from the slope of the triangular prism. Then, the heat Q1 from the imaging element 59 and the heat Q2 from the regulator 77 are transmitted concurrently and uniformly in the front and rear surfaces of the cover glass 65, respectively. As a result, the temperature difference between the front and rear surfaces of the cover glass 65 is suppressed to prevent dew condensation from occurring.

In addition, the slope of the triangular prism 55 is bonded to the regulator 77 and the other electronic component 80 substantially without any gap, so that the heat transmissibility can be improved on a large scale as compared with the case where the slope of the triangular prism 55 is bonded to the regulator 77 and the other electronic component 80 through a bonding agent layer with a predetermined thickness.

Even when the regulator 77 and the triangular prism 55 are bonded through a bonding agent with low viscosity, floating caused by the bonding layer can be prevented surely because the regulator 77 is pressed strongly onto the triangular prism 55 by the pressing force of the board. In this manner, increase of thickness in the bonding layer can be prevented by the pressing force of the circuit board 57. It is therefore possible to reduce the influence on the heat transmissibility between the regulator 77 and the triangular prism 55.

In addition, in this configuration, electronic components mounted on the circuit board 57 are used directly as heating sources without newly adding another heating component such as a heater. Accordingly, loss of energy can be prevented, and increase in number of components can be also prevented.

Without the necessity of performing predetermined timing control to particularly synchronize the driving of the regulator 77 with a trigger of the start timing to drive the imaging element 59, the driving of the imaging element 59 is automatically started concurrently with the start of the driving of the regulator 77. Thus, the driving start timing of the regulator 77 and that of the imaging element 59 can be synchronized easily.

When heat generated from the other electronic components 79 etc. is included in the heat Q2 from the regulator 77, the amounts of the heats Q1 and Q2 transmitted to the cover glass 65 can be further equalized to each other. Thus, occurrence of the temperature difference can be further reduced.

In addition, when the endoscopic apparatus 100 is in actual use after powered on, liquid may be delivered toward the observation window 37 from the nozzle 41 shown in FIGS. 2 and 3. At that time, the amount of heat taken by the delivered liquid from the observation window 37 is compensated with heat generated from the regulator 77 and the electronic component 80 (see FIG. 4) so as to prevent heat from escaping from the cover glass 65 to the observation window 37. Thus, dew condensation can be prevented from occurring due to liquid delivered during maneuver.

In addition, the regulator 77 and the second component mounting portion 71b of the circuit board 57 are disposed on the slope of the triangular prism 55. Accordingly, the space which has been a dead space on the back side of the triangular prism 55 can be put into effective use to contribute to the miniaturization of the endoscopic apparatus.

Further, the slope of the triangular prism 55 is partially covered with the regulator 77 and the electronic component 80. Accordingly, the filling amount of the bonding agent can be reduced so that the material cost can be reduced and the time required for solidifying the bonding agent in the manufacturing process can be also shortened. In addition, since the area of the bonding agent layer 89 with low heat conductivity can be reduced, heat of the imaging device whose temperature has risen can be prevented from being confined in the triangular prism 55, and the environmental temperature around the imaging element 59 can be prevented from rising. It is therefore possible to acquire low-noise image data.

In addition, the circuit board 57 which is a flexible printed circuit board can be assembled with such a simple work that one end portion of the circuit board 57 is pasted onto the slope of the triangular prism 55. It is therefore possible to simplify the manufacturing process.

According to this configuration, as described above, the regulator 77 brought into contact with the slope of the triangular prism 55 generates heat in sync with the driving of the imaging element 59. Thus, the temperature difference between the front and rear surfaces of the cover glass 65 disposed on the imaging element 59 through the air gap 67 can be prevented from occurring due to the temperature rise of the imaging element 59. In this manner, it is possible to surely prevent dew condensation from appearing in the surface of the cover glass 65. In addition, even when liquid is delivered toward the observation window 37 (see FIG. 2) in the endoscope front end portion, the influence of heat absorbed by the delivered liquid on the observation window can be compensated by the heat generated by the regulator 77 so that the heat absorbing effect can be prevented from being transmitted to the cover glass 65. Even in such a case, dew condensation in the cover glass 65 can be prevented surely. Accordingly, an image observed by the endoscopic apparatus can be always secured in good condition and with a wide field of view. Thus, endoscopic diagnosis can be performed rapidly and appropriately.

As described above, the invention is not limited to the aforementioned exemplary embodiment, but the invention also intends to be modified and applied by those skilled in the art based on the description of this specification and well-known techniques, and those modifications and applications are included in the scope of protection of the invention. In addition, this specification discloses the following matters.

(1) An endoscopic imaging device including:
an objective optical system which imports observation light from a subject;
an imaging element which captures an image of the observation light;
a transmissive protective substrate which is disposed on an imaging surface of the imaging element with an air gap interposed therebetween;
an optical member which is disposed between the objective optical system and the transmissive protective substrate to guide light from the objective optical system to the imaging surface; and
a circuit board which is disposed so that an area where an electronic component is mounted faces the optical member and the electronic component is brought into contact with an outer surface of the optical member.

According to this endoscopic imaging device, the optical member can be heated by heat generated from the electronic component so as to reduce the temperature difference between the front and rear surfaces of the transmissive protective substrate as a cause of dew condensation which may occur on the surface of the transmissive protective substrate. Thus, occurrence of dew condensation is prevented so that a good field of view can be always secured. In addition, since the electronic component is in contact with the optical member, the heat generated from the electronic component is transmitted to the optical member with high efficiency so that the temperature difference can be reduced more surely. Further, another component exclusive for heating is not necessarily disposed separately, and the heat of the electronic component mounted on the circuit board is used. Accordingly, it is possible to arrange the configuration with a low energy loss.

(2) An endoscopic imaging device according to the paragraph (1), wherein:
the area of the circuit board facing the optical member, excluding the surface in contact with the electronic component, is bonded to the optical member through a bonding agent layer.

According to the endoscopic imaging device, the bonding agent for the surface in contact with the electronic component can be saved. It is therefore possible to suppress the use amount of the bonding agent, and it is also possible to shorten the time required for solidifying the bonding agent in manufacturing.

(3) An endoscopic imaging device according to the paragraph (1) or (2), wherein:
the optical member is a triangular prism which changes an optical path at right angles, and the electronic component is brought into contact with a total reflection slope of the triangular prism.

According to the endoscopic imaging device, the electronic component is brought into contact with the total reflection slope of the triangular prism, so that the electronic component can be disposed in a space which has been a dead space on the back side of the triangular prism, to thereby contribute to the miniaturization of the device.

(4) An endoscopic imaging device according to any one of the paragraphs (1) through (3), wherein:
the electronic component is a regulator which outputs a constant voltage.

According to the endoscopic imaging device, the regulator which generates large heat is brought into the optical member so that the heat transmissibility to the optical member can be enhanced to reduce occurrence of the temperature difference.

(5) An endoscopic imaging device according to the paragraph (4), wherein:
the regulator outputs a drive signal for driving the imaging element.

According to the endoscopic imaging device, heat generated from the regulator can be obtained in sync with the heat generating timing of the imaging element. Thus, occurrence of the temperature difference can be reduced more surely.

(6) An endoscopic imaging device according to any one of the paragraphs (1) through (5), wherein:
the circuit board is a flexible printed circuit board.

According to the endoscopic imaging device, the circuit board mounted with the electronic component is a flexible printed circuit board. Accordingly, the circuit board can be disposed easily along the shape of the optical member so that the electronic component can be easily brought into contact with the optical member.

(7) An endoscopic imaging device according to the paragraph (6), wherein:

the circuit board includes at least a first board portion mounted with the imaging element, a second board portion connected to the first board portion through a first bending axis, and a third board portion connected to the second board portion through a second bending axis which is parallel to the first bending axis; and flexural rigidity in the second bending axis is higher than that in any other position of the circuit board.

According to the endoscopic imaging device, the third board portion can be pressed onto the optical member to improve the tight contact between the optical member and the electronic component. Thus, the heat transmissibility can be enhanced.

(8) An endoscopic imaging device according to the paragraph (6) or (7), wherein:

the circuit board includes a first board portion mounted with the imaging element, a second board portion connected to the first board portion through a first bending axis, a third board portion connected to the second board portion through a second bending axis which is parallel to the first bending axis, and a fourth board portion connected to the second board portion through a bending axis whose direction is different from that of each of the first and second bending axes;

the third board portion is bent in the second bending axis so as to be brought into contact with the optical member; and the second bending axis and the fourth board portion are disposed more closely to the imaging element than a distal end which is an end of the third board portion in contact with the optical member and which is far from the imaging element.

According to the endoscopic imaging device, the circuit board is folded to have such a layout so that the elastic repulsion of the third board portion in the second bending axis can be increased. In addition, the installation space of the circuit board can be reduced.

(9) An endoscopic apparatus including:

an endoscopic imaging device according to any one of the paragraphs (1) through (8), which is mounted on a front end portion of an endoscope to be inserted into a subject.

According to the endoscopic apparatus, observation can be always made with a good field of view while occurrence of dew condensation is suppressed.

(10) An endoscopic apparatus according to the paragraph (9), further including:

a nozzle which is disposed in the front end portion of the endoscope and which sprays liquid toward an observation window having an optical path connected to the objective optical system.

According to the endoscopic apparatus, dew condensation can be prevented from occurring in the transmissive protective substrate even when the objective optical system is cooled by liquid delivered from the nozzle.

What is claimed is:

1. An endoscopic imaging device comprising:
an objective optical system that imports observation light from a subject;
an imaging element that captures an image of the observation light;
a transmissive protective substrate that is disposed on an imaging surface of the imaging element with an air gap interposed therebetween;
an optical member that is disposed between the objective optical system and the transmissive protective substrate to guide light from the objective optical system to the imaging surface; and
a circuit board that is disposed so that an area where an electronic component is mounted faces the optical member and the electronic component is brought into contact with an outer surface of the optical member,
wherein the area of the circuit board facing the optical member, excluding the surface in contact with the electronic component, is bonded to the optical member through a bonding agent layer.

2. The endoscopic imaging device according to claim 1, wherein the optical member is a triangular prism which changes an optical path at right angles, and the electronic component is brought into contact with a total reflection slope of the triangular prism.

3. The endoscopic imaging device according to claim 1, wherein the electronic component is a regulator which outputs a constant voltage.

4. The endoscopic imaging device according to claim 1, wherein the circuit board is a flexible printed circuit board.

5. The endoscopic imaging device according to claim 4, wherein the circuit board includes at least a first board portion mounted with the imaging element, a second board portion connected to the first board portion through a first bending axis, and a third board portion connected to the second board portion through a second bending axis which is parallel to the first bending axis, and wherein flexural rigidity in the second bending axis is higher than that in any other position of the circuit board.

6. The endoscopic imaging device according to claim 5, wherein the circuit board further includes a fourth board portion connected to the second board portion through a bending axis whose direction is different from that of each of the first and second bending axes, wherein the third board portion is bent in the second bending axis so as to be brought into contact with the optical member, and wherein the second bending axis and the fourth board portion are disposed more closely to the imaging element than a distal end which is an end of the third board portion in contact with the optical member and which is far from the imaging element.

7. The endoscopic imaging device according to claim 4, wherein the circuit board includes a first board portion mounted with the imaging element, a second board portion connected to the first board portion through a first bending axis, a third board portion connected to the second board portion through a second bending axis which is parallel to the first bending axis, and a fourth board portion connected to the second board portion through a bending axis whose direction is different from that of each of the first and second bending axes, wherein the third board portion is bent in the second bending axis so as to be brought into contact with the optical member, and wherein the second bending axis and the fourth board portion are disposed more closely to the imaging element than a distal end which is an end of the third board portion in contact with the optical member and which is far from the imaging element.

8. An endoscopic imaging device comprising:
an objective optical system that imports observation light from a subject;
an imaging element that captures an image of the observation light;

a transmissive protective substrate that is disposed on an imaging surface of the imaging element with an air gap interposed therebetween;

an optical member that is disposed between the objective optical system and the transmissive protective substrate to guide light from the objective optical system to the imaging surface; and a circuit board that is disposed so that an area where an electronic component is mounted faces the optical member and the electronic component is brought into contact with an outer surface of the optical member, wherein the electronic component is a regulator which outputs a constant voltage, and wherein the regulator outputs a drive signal for driving the imaging element.

9. An endoscopic apparatus comprising:

a front end portion that is inserted into a subject; and an endoscopic imaging device that is mounted on the front end portion and that includes:

an objective optical system that imports observation light from a subject;

an imaging element that captures an image of the observation light;

a transmissive protective substrate that is disposed on an imaging surface of the imaging element with an air gap interposed therebetween;

an optical member that is disposed between the objective optical system and the transmissive protective substrate to guide light from the objective optical system to the imaging surface; and a circuit board that is disposed so that an area where an electronic component is mounted faces the optical member and the electronic component is brought into contact with an outer surface of the optical member, wherein the area of the circuit board facing the optical member, excluding the surface in contact with the electronic component, is bonded to the optical member through a bonding agent layer.

10. The endoscopic apparatus according to claim 9 further comprising a nozzle that is disposed in the front end portion and that sprays liquid toward an observation window having an optical path connected to the objective optical system.

11. An endoscopic apparatus comprising:

a front end portion that is inserted into a subject; and an endoscopic imaging device that is mounted on the front end portion and that includes:

an objective optical system that imports observation light from a subject;

an imaging element that captures an image of the observation light;

a transmissive protective substrate that is disposed on an imaging surface of the imaging element with an air gap interposed therebetween;

an optical member that is disposed between the objective optical system and the transmissive protective substrate to guide light from the objective optical system to the imaging surface; and a circuit board that is disposed so that an area where an electronic component is mounted faces the optical member and the electronic component is brought into contact with an outer surface of the optical member, wherein the electronic component is a regulator which outputs a constant voltage, and wherein the regulator outputs a drive signal for driving the imaging element.

* * * * *